United States Patent [19]
Farinas et al.

[11] Patent Number: 5,928,666
[45] Date of Patent: Jul. 27, 1999

[54] CRYSTALLINE FORM OF ESTRADIOL AND PHARMACEUTICAL FORMULATIONS COMPRISING SAME

[75] Inventors: Kathleen C. Farinas, San Carlos; Yalia Jayalakshmi, Palo Alto, both of Calif.; Susanne M. Lee, Albany, N.Y.; Pravin L. Soni, Sunnyvale, Calif.

[73] Assignee: Cygnus Inc., Redwood City, Calif.

[21] Appl. No.: 08/968,769

[22] Filed: Nov. 10, 1997

Related U.S. Application Data

[60] Provisional application No. 60/030,524, Nov. 12, 1996.

[51] Int. Cl.⁶ .............................. A61K 9/70; A61K 9/26; A61K 31/56
[52] U.S. Cl. ..................... 424/449; 424/448; 424/469; 514/182; 552/625
[58] Field of Search ..................................... 424/487, 486, 424/448, 449, 464–465, 469; 514/182, 843, 946–947; 552/625

[56] References Cited

U.S. PATENT DOCUMENTS 5,827,245  10/1998  Horstmann et al. .

*Primary Examiner*—Edward J. Webman
*Attorney, Agent, or Firm*—Angela P. Horne; Barbara G. McClung

[57] ABSTRACT

The present invention is directed to a stable crystalline form of estradiol suitable for incorporation into pharmaceutical formulations. The invention further provides methods of preparing said crystalline form of estradiol. The invention further provides pharmaceutical formulations comprising said crystalline form of estradiol. The invention further provides a method of treatment of an individual in need of such administration by the transdermal administration of estradiol from a polymeric matrix comprising the crystal structure of estradiol of the present invention.

18 Claims, 1 Drawing Sheet

CRYSTALLINE FORM OF ESTRADIOL AND PHARMACEUTICAL FORMULATIONS COMPRISING SAME

CROSS-REFERENCE TO RELATED APPLICATIONS

This application claims priority to U.S. provisional application Ser. No. 60/030,524 filed Nov. 12, 1996, from which application priority is claimed pursuant to 35 U.S.C. § 120.

BACKGROUND OF THE INVENTION

Estradiol (estra-1, 3, 5(10)-triene-3, 17β-diol or 17β-estradiol) is a pharmaceutical compound commonly administered in hormone replacement therapy regimens. The designation 17α-estradiol was incorrectly used prior to ca. 1952. (*Estradiol* by Eugene A. Salole in *Analytical Profiles of Drug Substances*, K.Florey, ed. (1986) Academic Press, Inc. 15:283–318). Estradiol is known to form several crystal structures. The most stable form of estradiol is estradiol hemihydrate (E2-HH). Two anhydrous structures have been reported in the literature. Estradiol also forms solvates with organic solvents such as methanol and ethanol.

A common method for characterizing estradiol crystalline forms is provided by X-ray powder diffraction data. Excluding solvates other than hydrates, there are three sets of x-ray powder diffraction (XRD) data for 17β-estradiol published in the literature.

The XRD pattern for the most stable anhydrous crystal structure is provided in the Joint Committee on Powder Diffraction Standards (JCPDS) 38-1522. The sample was prepared by heating the hemihydrate at 170° C. for several hours, presumably at ambient pressure.

The first set of data relating to E2-HH was collected by Parsons et al. (reference). JCPDS File 10-851 lists the same 30 diffraction peaks as Parsons, et al. with slightly different intensities. JCPDS describes 10-851 as alpha-E2-HH, Chemical Abstracts Service (CAS) registry number 50-28-2 possessing a molecular weight of 281.39 and a melting point of 176–179° C. It is believed that the naming of the compound in this reference is incorrect in accordance with the practice at the time as discussed above. The second set of data for E2-HH is JCPDS File 10-549. This is listed as P-Estradiol (1, 3, 5(10)-estratriene-3, 17βdiol) with a CAS number of 50-28-2. This data is consistent with the description of E2-HH provided by Salole. The structure is orthorhombic with crystallographic parameters (measured in angstroms) of a=12.04, b=19.26, c=6.642, A=0.6251, C=3449 (orthorhombic), similar to values listed by Hospital (1972) of a=12.055±0.003, b=19.280±0.003, c=6.632±0.002 (orthorhombic).

Resetarits, et al. (Int'. J. Pharma. (1979) 2:113–123) also made a crystal with a "relatively rapid recrystallization" process from absolute ethanol at 37° C. The Raman spectrum and x-ray diffraction pattern were similar to that from the hemihydrate.

The present invention provides a stable crystalline form of estradiol distinguishable from the foregoing crystal structures of estradiol based on XRD data and having greater solubility and thermodynamic activity with respect to E2-HH suitable for incorporation into pharmaceutical formulations.

SUMMARY OF THE INVENTION

The present invention is directed to a stable crystalline form of estradiol suitable for incorporation into pharmaceutical formulations. The invention further provides methods of preparing said crystalline form of estradiol. The invention further provides pharmaceutical formulations comprising said crystalline for m of estradiol. The invention further provides a method of treatment of an individual in need of such administration by the transdermal administration of estradiol from a polymeric matrix comprising the crystal structure of estradiol of the present invention.

Additional objects, advantages and novel features of the invention will be set forth in part in the description which follows, and in part will become apparent to those skilled in the art upon examination of the following, or may be learned by practice of the invention.

DETAILED DESCRIPTION OF THE INVENTION

Figure 1:
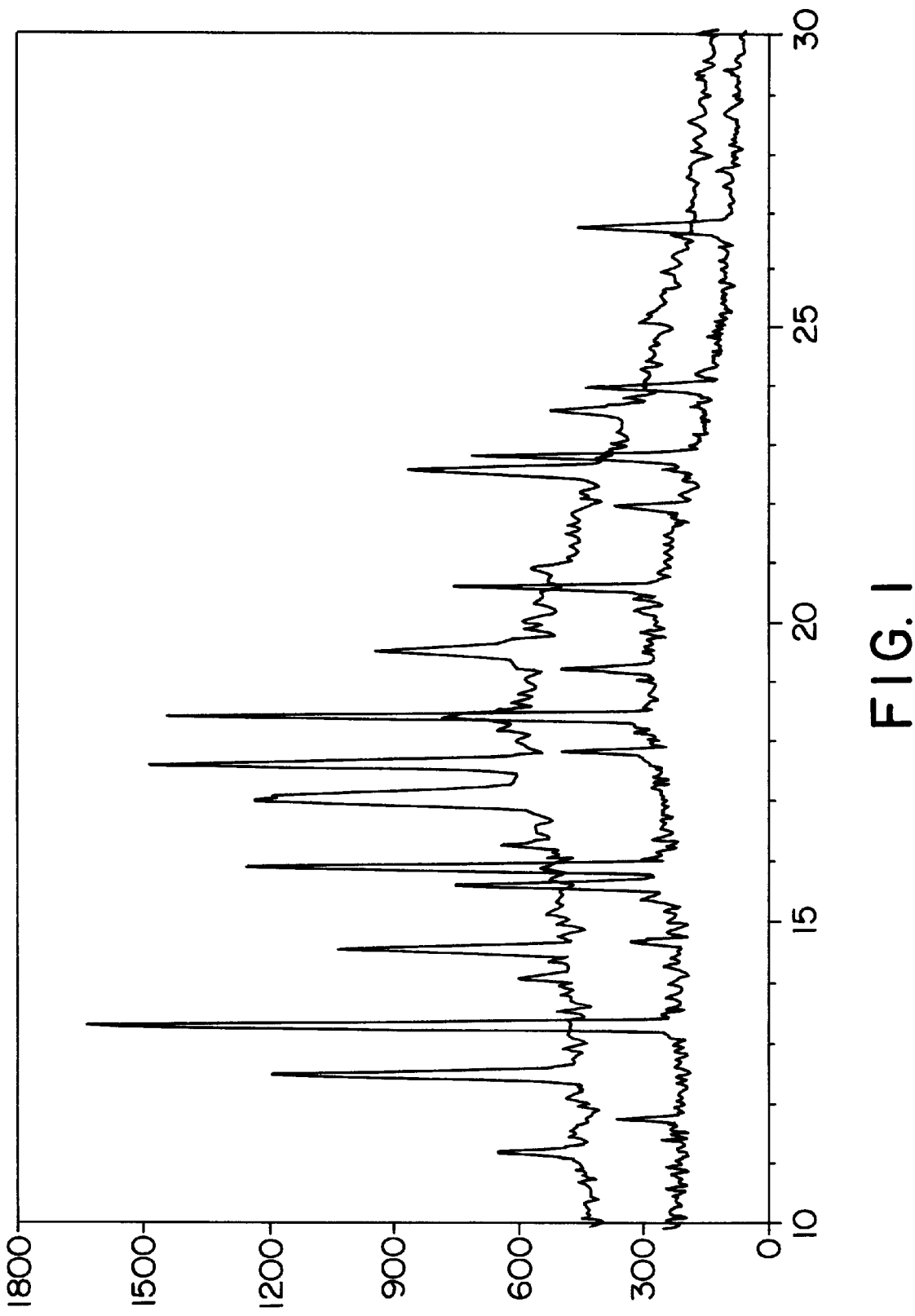
FIG. 1 is a powder X-ray diffraction pattern for Crystal X crystalline estradiol and for E2-HH crystalline estradiol. The upper diffractogram represents Crystal X while the lower diffractogram represents E2-HH. Diffraction angle (2θ) is plotted on the x-axis and x-ray photon counts are plotted on the y-axis.

Before describing the present invention in detail, it is to be understood that this invention is not limited to particular transdermal drug delivery device configurations, particular drug/vehicle formulations, or the like, as such may vary. It is also to be understood that the terminology used herein is for the purpose of describing particular embodiments only, and is not intended to be limiting.

It must be noted that, as used in this specification and the appended claims, the singular forms "a", "an" and "the" include plural referents unless the content clearly dictates otherwise. Thus, for example, reference to "a permeation enhancer" includes a mixture of two or more permeation enhancers, reference to "an excipient" or "a vehicle" includes mixtures of excipients or vehicles, reference to "an adhesive layer" includes reference to two or more such layers, and the like.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein.

The present invention provides a stable crystalline form of estradiol characterized by possessing at least one diffraction peaks having a 2θ angles of 11.2°±0.2°, 12.7°±0.2°, 17.4°±0.2° or 19.6°±0.2 (hereinafter referred to as "Crystal X").

For purposes of the present invention. the term "estradiol" is defined as estra-1, 3, 5(10)-triene-3, 17β-diol or 17β-estradiol.

For purposes of the present invention, the term "stable" indicates that the crystal structure is preserved over a time period of from weeks to years.

For purposes of the present invention, the term "diffraction peaks" means the 2θ angles produced by powder X-ray diffraction studies in accordance with techniques known in the art of X-ray crystallography. θ is defined in the Bragg Equation and is directly related to the d-spacing between lattice planes in the crystal for a particular wavelength (preferably 1.54A as used in the preferred practice of the invention as exemplified herein).

A comparison of the diffraction peaks available in the literature for estradiol crystal structures is summarized in Table 1 which demonstrates the difference between the crystal structure of estradiol of the present invention (Crystal X) and the art.

TABLE 1

Comparison of 2θ Angles of Crystal X v. 2θ Angles of Other Estradiol Crystals

| Crystal X | Standard Deviation | Literature Values |
|---|---|---|
| 11.21 | .03 | 11.588 anhydrous |
| 12.70 | .06 | 13.184 HH10-851 |
|  |  | 13.344 HH10-549 |
| 17.37 | .05 | 17.724 HH10-851 |
|  |  | 17.76 HH10-549 |
| 19.63 | .06 | 19.153 HH10-851 |
|  |  | 19.237 HH10-549 |
|  |  | 19.195 anhydrous |

As can be seen from the above XRD data, Crystal X represents a crystalline form of estradiol not previously described in the art.

The Crystal X crystalline form of estradiol possesses increased thermodynamic activity with respect to E2-HH. Consequently, Crystal X provides an advantage in the preparation of pharmaceutical formulations comprising Crystal X especially transdermal drug delivery matrices. When Crystal X crystals are prepared in transdernal drug delivery formulations, the inherent increase in activity due to the higher thermodynamic activity of the Crystal X crystal versus E2-HH provides for increased flux. For example, equilibrated matrices containing Crystal X and E2-HH crystals were prepared in substantial accordance with the teaching of Example 7 herein and assayed for permeation through a Silastic membrane. The results presented in Table 2 below demonstrate that matrices containing Crystal X crystals provides a substantially greater flux of estradiol than a matrix containing E2-HH.

TABLE 2

Comparison of Flux of Crystal X v. E2-HH ($\mu g/cm^2/hr$)

| Time (hrs) | Crystal X | E2-HH |
|---|---|---|
| 2.5 | 0.132 | 0.080 |
| 8.375 | 0.238 | 0.139 |
| 17.625 | 0.216 | 0.142 |
| 27.75 | 0.220 | 0.146 |

From the above data, the average flux for Crystal X is 0.22 and the average flux for E2-HH is 0.14. This gives a flux ratio of approximately 1.6:1, Crystal X:E2-HH.

Crystal X also possesses increased solubility with respect to E2-HH. The increased solubility of the Crystal X crystals provides an advantage in the preparation of polymeric matrices for incorporation into transdermal drug delivery systems. Ideally, the rate of crystallization of estradiol in a supersaturated matrix should be slow to avoid the formation of crystals which reduces flux. The term "supersaturation ratio" is defined as the ratio: (concentration of estradiol hemihydrate dissolved in the formulation/solubility of estradiol hemihydrate in the formulation at the storage conditions). If the supersaturation ratio is <12, the tendency is to form hemihydrate crystals. However, if the supersaturation ratio >12, the formation of Crystal X is favored. The rate of crystallization increases with the supersaturation ratio. For a given drug loading, the supersaturation ratio for hemihydrate is higher than that for Crystal X since the solubility of Crystal X is much higher relative to the solubility of hemihydrate. Hence the rate of crystallization is slowed when the supersaturation is approximately equal to or greater than 12. Consequently, a higher drug flux is achieved. See Example 8. The slower rate of crystallization is advantageous in the preparation of a transdermal estradiol formulation in that the supersaturation ratio >12 favors the formation of Crystal X. Under such conditions. the formation of crystalline estradiol is not favored such that a supersaturated non-crystalline matrix is preserved.

It would be expected that, since the flux value at the end of the flux profile for Crystal X is about 2 times higher than for E2-HH, the thermodynamic activity and solubility of Crystal X should also be about 2 times higher than for E2-HH. In order to verify this conclusion and to demonstrate that Crystal X possesses a higher thermodynamic activity and solubility than estradiol HH, a partitioning experiment was performed with a solid donor/receiver system in accordance with the teaching of Example 6 below. The flux experiements were performed at 32° C. under wet conditions, therefore the solubility experiements were performed under substantially the same conditions as the flux studies provided above. The results of these experiments are summarized in Table 3 below:

TABLE 3

Solubility of E2-HH and Form-X at 32° C. and 60° C. in Durotak 2287

| Crystal Structure | Equilibration Condition | Avg. Solubility |
|---|---|---|
| E2-HH | 32° C. wet | 0.38 wt % |
| Crystal X | 32° C. wet | 0.68 wt % |

The solubility ratio of approximately 2 (1.8:1) was obtained which is accordance with the values expected from the flux data presented.

The present invention further provides a method for preparing Crystal X said method comprising the steps of:
a) prepare a supersaturated suspension of estradiol hemihydrate crystals in an adhesive and solvent;
b) remove the solvent;
c) heat the suspension to a temperature sufficient to dissolve the estradiol hemihydrate crystals in the adhesive;
d) transfer to conditions wherein the supersaturation ratio is greater than or equal to about 12 to recrystallize the estradiol.

The present invention further provides an alternate method of preparing Crystal X, said method comprising the steps of:
a) prepare a supersaturated suspension of estradiol hemihydrate crystals in an adhesive and solvent;
b) remove the solvent;
c) heat the suspension of to a temperature sufficient to dissolve the estradiol hemihydrate crystals in the adhesive;
d) transfer to conditions of approximately 32° C. and 80% relative humidity to recrystallize the estradiol.

The present invention further provides an alternative method for preparing crystals of Form X from micronized E2-HH crystals said method comprising the steps of:
a.) preparing a sample of pure micronized E2-HH in an sealed container in the absence of extraneous water;
b.) heating the sample to the melting temperature of the micronized E2; and c.) cooling the sample at a controlled rate so as to form Crystal X.

In the preferred practice of the invention, the pure micronized E2-HH is heated in an O-ring sealed aluminum or steel DSC pan in a differential scanning calorimeter. The term "in the absence of extraneous water", is meant to indicate that no water other than the ambient humidity and the water in the crystals is present and that no additional water is added. In the preferred practice of the invention as exemplified herein the sample is cooled at approximately 5° C. per minute. In this manner, one is provided with Crystal X in the absence of a polymeric matrix. Crystal X produced in accordance with this method therefore may be readily incorporated into a variety of pharmaceutical formulations such as tablets, caplets, capsules further comprising standard pharmaceutical excipients such as carboxymethyl cellulose, croscarmellose, etc. for oral administration.

For purposes of the present invention, the term "adhesive" means pressure-sensitive adhesives which are physically and chemically compatible with estradiol. and the carriers and vehicles employed. Such adhesives include, for example, polysiloxanes, polyisobutylenes. polyacrylates, polyurethanes, plasticized ethylene-vinyl acetate copolymers, low molecular weight polyether amide block polymers (e.g., PEBAX), tacky rubbers such as polyisobutene, polystyrene-isoprene copolymers, polystyrene-butadiene copolymers, and mixtures thereof. Presently preferred adhesive materials for use as reservoir layer are acrylates, silicones and polyisobutylenes. Also preferred as a reservoir material is Durotak 87-2287 acrylate adhesive. Also preferred are the reservoir materials described in commonly assigned U.S. Pat. No. 5,252,334 to Chiang et al., i.e., combinations of acetate-acrylate copolymers (such as may be obtained under the trademarks GELVA® 737 and GELVA® 788 from Monsanto Chemical Co.). Alternatively, pressure-sensitive, hot melt adhesives can be used, typically employing a melt coating or extrusion process. Examples of such hot melt, pressure-sensitive adhesives are adhesives based on styrene block copolymers, acrylics, polyisobutylenes. In the preferred practice of the invention as exemplified herein, the adhesive is an acrylate, polyisobutylene, or silicone adhesive matrix.

For purposes of the present invention, the term "solvent" means solvents generally used with adhesives as described above which are compatible-with estradiol.

For purposes of the present invention, the term "a supersaturated suspension" is understood to mean a condition wherein the total (dissolved plus crystalline) concentration of estradiol hemihydrate in the adhesive is greater than the quantity of estradiol hemihydrate soluble under standard conditions.

For purposes of the present invention, the term "supersaturation ratio" is defined as the ratio: (concentration of estradiol hemihydrate dissolved in the formulation/solubility of estradiol hemihydrate in the formulation at the storage conditions). In order to obtain supersaturation ratios, the solubility data of estradiol hemihydrate was obtained as a function of temperature using power-compensated DSC without excess water. Cogan-Farinas, et al. (1995) 24th NATAS Conf. Proc. pp. 567. This solubilty data was utilized to calculate supersaturation ratios for the purposes of the present invention and as provided in Examples 1 and 2 herein. It is understood by those of skill in the art that the term "solubility of estradiol in the formulation at the storage condition" is a function of temperature and humidity and may readily be experimentially determined. Thus, supersaturation ratios for "wet" conditions may be readily determined by DSC methods known to those of skill in the art.

It is another object of the invention to provide a pharmaceutical formulation comprising Crystal X for administering a pharmaceutically effective quantity of estradiol to a human subject. Preferred pharmaceutical formulations comprising Crystal X are polymeric matrix formulations for the systemic administration of estradiol in hormone replacement therapy, the treatment of osteoporosis or in combination with other hormones such as a testosterone, or in combination with a progestin for contraceptive applications. Such polymeric matrices may be used for transdermal application or for subcutaneous "implant" formulations.

In the preferred practice of the invention, the pharmaceutical formulation is a monolithic polymeric matrix for incorporation in a transdermal drug delivery system for delivering a pharmaceutically effective quantity of estradiol to a subject over an area of intact skin. Such a structure is generally termed a "monolithic" transdermal system because the reservoir layer doubles as the adhesive which affixes the device to the skin. The reservoir layer in doubles as the means for containing drug and as an adhesive for securing the device to the skin during use. The reservoir layer is comprised of an adhesive material as described above, and will generally range in thickness from about 10 to about 300 microns, preferably approximately 75 microns.

By "transdermal" delivery, applicants intend to include both transdermal (or "percutaneous") and transmucosal administration, i.e., delivery by passage of a drug through the skin or mucosal tissue and into the bloodstream.

By an "effective" amount of a drug is meant a nontoxic but sufficient amount of the drug to provide the desired therapeutic or prophylactic effect. An "effective" amount of a permeation enhancer as used herein means an amount that will provide the desired increase in skin permeability and, correspondingly, the desired depth of penetration rate of administration, and amount of drug delivered.

By "predetermined area of skin" is intended a defined area of intact unbroken living skin or mucosal tissue. That area will usually be in the range of about 5 $cm^2$ to about 100 $cm^2$, more usually in the range of about 20 $cm^2$ to about 60 $cm^2$. However, it will be appreciated by those skilled in the art of transdermal drug delivery that the area of skin or mucosal tissue through which drug is administered may vary significantly, depending on patch configuration, dose, and the like. Also, as noted above, the present technology enables preparation of generally smaller patches, typically in the range of about 5 $cm^2$ to about 20 $cm^2$.

The formulation may also include standard carriers or vehicles useful for facilitating drug delivery, e.g., stabilizers, antioxidants, anti-irritants, crystallization inhibitors (such as polyvinylpyrrolidone, cellulosic polymers, polyethylene oxide, polyvinyl alcohol, polyacrylic acid, gelatins, cyclodextrins, silica and the like). Cross-linking agents may also be included which will incorporate into the polymeric matrix. "Carriers" or "vehicles" as used herein refer to carrier materials suitable for transdermal drug administration, and include any such materials known in the art, e.g., any liquid, gel, solvent, liquid diluent, solubilizer, or the like, which is nontoxic and which does not interact with other components of the composition in a deleterious manner. Examples of suitable carriers for use herein include silicone, liquid sugars, waxes, petroleum jelly, and a variety of other materials. The term "carrier" or "vehicle" as used herein may also refer to stabilizers, crystallization inhibitors, or other types of additives useful for facilitating transdermal drug delivery.

Skin permeation enhancers may also be present in the drug formulation, although, as explained above, the present manufacturing technique reduces the need for enhancers by virtue of increasing the rate of drug release. "Penetration enhancement" or "permeation enhancement" as used herein relates to an increase in the permeability of skin to a pharmacologically active agent, i.e., so as to increase the rate at which the drug permeates through the skin and enters the bloodstream. The enhanced permeation effected through the use of such enhancers can be observed by measuring the rate of diffusion of drug through animal or human skin using a conventional Franz diffusion cell apparatus. If enhancers are incorporated in the device, they will generally represent on the order of approximately 1 wt. % to 25 wt. % of the drug formulation. Suitable enhancers include, but are not limited to, dimethylsulfoxide (DMSO), dimethyl formamide (DMF), N,N-dimethylacetamide (DMA), decylmethylsulfoxide ($C_{10}$MSO), polyethylene glycol monolaurate (PEGML), propylene glycol (PG), propylene glycol monolaurate (PGML), glycerol monolaurate (GML), methyl laurate (ML), lauryl lactate (LL), isopropyl myristate (IPM), terpenes such as menthone, $C_2$–$C_6$ diols, particularly 1,2-butanediol, lecithin, the 1-substituted azacycloheptan-2-ones, particularly 1-n-dodecylcyclazacycloheptan-2-one (available under the trademark Azone® from Whitby Research Incorporated, Richmond, Va.), alcohols, and the like. Vegetable oil permeation enhancers, as described in commonly assigned U.S. Pat. No. 5,229,130 to Sharma, may also be used. Such oils include, for example, safflower oil, cotton seed oil and corn oil. It is further understood that combinations of the above enhancers may also be included in the formulation.

Preferred drug formulations, i.e., the drug-containing composition which is loaded into the drug reservoir, will typically contain on the order of about 0.1 wt. % to 20 wt. % estradiol hemihydrate, preferably about 1 wt. % to 10 wt. % estradiol hemihydrate, with the remainder of the formulation representing other components such as enhancers, vehicles or the like.

The present invention also provides a transdermal drug delivery system comprising the drug delivery matrix having a first surface and a second surface as described above further comprising a backing layer applied to said first surface and a release liner applied to said second surface. The backing layer functions as a structural element of the device and provides the device with much of its flexibility, drape and, preferably, occlusivity. The material used for the backing layer should be inert and incapable of absorbing or reacting with the drug, enhancer or other components of the pharmaceutical composition contained within the device. The backing is preferably made of one or more sheets or films of a flexible elastomeric material that serves as a protective covering to prevent loss of drug and/or vehicle via transmission through the upper surface of the device, and will preferably impart a degree of occlusivity to the device, such that the area of the skin covered on application becomes hydrated. The material used for the backing layer should permit the device to follow the contours of the skin and be worn comfortably on areas of skin such as at joints or other points of flexure, that are normally subjected to mechanical strain with little or no likelihood of the device disengaging from the skin due to differences in the flexibility or resiliency of the skin and the device. Examples of materials useful for the backing layer are polyesters, polyethylene, polypropylene, polyurethanes and polyether amides. The layer is preferably in the range of about 15 microns to about 250 microns in thickness, and may, if desired, be pigmented, metallized, or provided with a matte finish suitable for writing.

The release liner is a disposable element which serves to protect the device prior to application. Typically, the release liner is formed from a material impermeable to the drug, vehicle(s), enhancer(s) and/or adhesive(s), and which is easily stripped from the contact adhesive. Release liners are typically treated with silicone or fluorocarbons. Silicone-coated polyester is presently preferred.

Any of the transdermal drug delivery devices manufactured using the present technique may also be provided with a release rate controlling membrane to assist in controlling the flux of drug and/or vehicle from the device. Such a membrane will be present in a drug delivery device beneath and typically immediately adjacent to the drug reservoir, and generally between the drug reservoir itself and an adhesive layer which affixes the device to the skin. Representative materials useful for forming rate-controlling membranes include polyolefins such as polyethylene and polypropylene, polyamides, polyesters, ethylene-ethacrylate copolymer, ethylene-vinyl acetate copolymer, ethylene-vinyl methylacetate copolymer, ethylene-vinyl ethylacetate copolymer, ethylene-vinyl propylacetate copolymer, polyisoprene, polyacrylonitrile, ethylene-propylene copolymer, and the like. A particularly preferred material useful to form the rate controlling membrane is ethylene-vinvl acetate copolymer.

The present invention further provides a method of administering estradiol to a human subject in need of such treatment by the application of a transdermal drug delivery system comprising Crystal X to the skin or mucosal surface of the subject in need of treatment. As illustrated above, Crystal X may be readily incorporated into pharmaceutical formulations. particularly transdermal drug delivery systems. As further indicated, the transdermal drug delivery systems comprising Crystal X are useful for the treatment of animals, particularly human subjects, particularly in light of the increased thermodynamic activity, solubility and flux derived from transdermal drug delivery systems comprising Crystal X. Methods of transdermal administration of estradiol are well known in the art as noted in Casper, et al., U.S. Pat. No. 5,422,119 issued Jun. 6, 1995, Casper, et al., U.S. Pat. No. 5,256,421 issued Oct. 26, 1993 and Chiang, et al., U.S. Pat. No. 5,252,334, the entire teachings of which are herein incorporated by reference. The normal dosage range for administration of estradiol in a hormone replacement therapy regiment is that amount generally required to produce a blood level of about 30 ng/L, while slightly higher blood levels (approximately 40 ng/L) are utilized for the treatment of osteoporosis. Blacker, et al. (1996) Clin. Drug Invest 11:339–346. Lower quantities of Crystal X are included in such formulations as compared to conventional estradiol transdermal formulations owing to the higher thermodynamic activity of Crystal X.

It will be readily apparent to those of skill in the art that the pharmaceutical formulations incorporating Crystal X may also include a progestin for the preparation of pharmaceutical formulations for contraceptive applications as described in Chien, et al., U.S. Pat. Nos. 4,906,169 issued Mar. 6, 1990 and 5,023,084 issued Jun. 11, 1991 and Wright, et al. U.S. Pat. No. 4,948,593 issued Aug. 14, 1990 the entire teachings of which are hereby incorporated by reference. Preferred progestins useful for incorporation into such formulations are norethindrone, norethindrone acetate, d-norgestrel, and norgestimate. Again, lower quantities of Crystal X are included in such formulations as compared to conventional contraceptive formulations owing to the higher thermodynamic activity of Crystal X.

The present invention further provides methods for manufacturing transdermal systems comprising Crystal X, said method comprising the steps of:

a) preparing a supersaturated suspension of estradiol hemihydrate crystals in an adhesive and solvent;

b) casting a substantially uniform film of the suspension of step (a) onto a backing layer;

c) removing the solvent;

d) applying a layer of release liner to the exposed surface of said film;

e) pouching the film;

f) heating the suspension to a temperature sufficient to dissolve the estradiol hemihydrate crystals in the adhesive during processing step (b), (c) (d) or (e) to produce a solution of the estradiol hemihydrate in the adhesive;

g) equilibrating said solution under conditions wherein the supersaturation ratio is greater than or equal to about 12.

The term "pouching" refers to the placement of the film produced in a water impermeable container. In the preferred practice of the invention, the water impermeable container is formed from of a heat sealed polymeric film envelope. In the preferred practice of the invention, the envelope is formed from and aluminized foil material such as #8630380 48 gauge aluminized foil (commercially available from American National Can Co.). In the preferred practice of the invention, the suspension is heated after removal of the solvent. In the most preferred practice of the invention, the suspension is heated after pouching.

EXAMPLES

It is to be understood that while the invention has been described in conjunction with the preferred specific embodiments thereof, that the description above as well as the examples which follow are intended to illustrate and not limit the scope of the invention. Other aspects, advantages and modifications within the scope of the invention will be apparent to those skilled in the art to which the invention pertains.

In the following examples, efforts have been made to ensure accuracy with respect to numbers used (e.g. amounts, temperature, etc.) but some experimental error and deviation should be accounted for. Unless indicated otherwise, temperature is in degrees ° C. and pressure is at or near atmospheric.

Materials

Micronized estradiol hemihydrate, USP grade, was obtained from Diosynth.

DURO-TAK® 87-2287 is an acrylic pressure sensitive adhesive commercially available from National Starch and Chemical Company and contains 50 wt. % ethyl acetate solvent which is removed during sample preparation.

Silicone 4201 adhesive is commercially available from by Dow Corning and contains 35 wt. % heptane solvent.

The PIB blend utilized in the preferred practice of the invention as exemplified herein contains a ratio of 1:5:4 of HMW PIB (Exxon Vistanex® MML-100, M.W. 1,060,000–1,440,000):LMW PIB (Exxon Vistanex® LM-MS-LC, M.W. 42,600–46,100):polybutene (Amoco Indopol® H-1900, M.W. 2300) and is prepared in a solution with 60% hexane.

3-EST-A-S242M polyester film with silicone release layer (commercially available from Release Internation) films were used as release liners when the adhesive is contacting the release side and backing materials when the adhesive is contacting the non-release side.

10 mil Silastic® (polydimethyl siloxane, non-reinforced, Rx medical grade) membrane is commercially available from Dow Corning Corporation (Midland, Mi. 48640).

Methods

Flux Measurement:

Measurement of estradiol flux was determined by drug flux through a 10 mil Silastic membrane in a modified Franz diffusion cells in substantial accordance with the following procedure. The adhesive matrix systems were peeled off the polyester release liner and placed on top of the Silastic membrane. Gentle pressure was applied to insure full contact between the drug adhesive layer and membrane. The membrane with the prototype system was then mounted carefully between the donor and the receiver compartments. The receiver compartment was filled nanopure water and the temperature was maintained at 32° C.±1° C. throughout the experimental period. Samples of receiver content was withdrawn and replaced with fresh buffer. Samples were assayed by HPLC.

Flux determination:

Membrane flux ($mg/cm^2/hr$) was determined by evaluating the cumulative flux of drug through a Silastic membrane over a given period of time and dividing by the time period. After steady state had been established, the flux values corresponding to steady state were averaged to obtain the flux value.

Determination of solubility:

The determination of estradiol solubility in PIB blend and silicone adhesive matrices was determined in accordance with the differential scanning calorimetry (DSC) method described by Theeuwes, et al (1974) J. Pharm. Sci. 63:427. The determination of solubility in Durotak acrylic adhesives was determined in accordance with the teaching of Example 6 below.

XRD system information:

All experiments were performed using a Siemens General Area Detector Diffraction System (GADDS) commercially available from the Siermens Corporation with a 2.2 kW Copper sealed tube x-ray source. The detector was a high stability/throughput/resolution area detector (HI-STAR) used in the 512×512 pixel mode. This is a two dimensional detector system with a multiwire proportional chamber and 11.5 cm diameter concave beryllium window. A graphite monochromator was placed between the x-ray source and the sample to permit only the CuK(alpha) radiation to impinge on the sample. A 0.8 mm diameter collimator was used to restrict the x-ray beam to less than the width of the Crystal X crystalline region. Standard operating conditions were an accelerating power of 45 kV and 35 mA for most of the samples. Alternatively operating conditions were 40 kV and 30 mA. Data collection times varied from 300 seconds to 600 seconds.

XRD Sample Preparation

Sample preparation depended on whether the Crystal X crystals were in adhesive or were made from micronized E2. The adhesive matrix containing Crystal X were mounted onto an aluminum foil using the adhesive side of the matrix. Aluminum X-ray diffraction peaks are far removed in $2\theta$ angles from the region of interest. This assembly was supported at the edges by a donut shaped washer. Crystal X region is centered with respect to the x-ray beam. The crystalline samples produced directly from the micronized estradiol powder (Example 9) were attached to the closed end of a small capillary tube by coating the tube with a thin film of vaseline. These samples were mounted in such a way that the x-rays only passed through the crystals and not through the capillary tube.

Example 1
Preparation of E2-HH in Acrylate Adhesive Matrix Laminates Under Dry Conditions Laminates comprising a variety of concentrations (wt. % estradiol based on estradiol and adhesive solids) were prepared. Appropriate amounts of micronized estradiol hemihydrate were added to DURO-TAK® 87-2287 containing ethyl acetate in order to prepare the desired concentrations of estradiol in adhesive solids. As utilized in the description of the present invention "dry" is used to indicate that no special means were adopted to maintain a particular humidity, but rather that prevailing atmospheric humidity conditions were present. Additional ethyl acetate (up to twice the amount of estradiol hemihydrate) was added to the higher concentration samples in order to reduce the wet sample viscosity to aid mixing. The samples were mixed on a rotator overnight. In all cases, the resultant mixture contained a dispersion of crystalline estradiol in wet adhesive. Laminates were drawn down on the release side of 3-EST-A-S242M film to a thickness of approximately 110 microns. The solvent was removed by drying in an oven at 70° C. for 1.5 hours. A second layer of 3-EST-A-S242M film was laminated onto the adhesive, release side contacting adhesive, for storage of the laminates. The laminates were die cut and placed in #8630380 48 gauge aluminized foil pouch material.

Example 2
Conversion of E2-HH to Crystal X in Acrylate Adhesive Matrix Laminates Under Dry Conditions:

The laminates prepared in Example 1 above were then heated to melt the E2-HH crystals in the adhesive. The temperature should be at least about 10 degrees in excess of the temperature at which the concentration is soluble in the matrix. The exposure should be for a period of about 20 minutes. When these samples are heated to a temperature above the temperature at which the concentration is soluble in the matrix, the samples become a single phase of drug dissolved in adhesive as is evidenced by their transparent appearance. The temperature at which a 20 wt % concentration of estradiol in DURO-TAK® 87-2287 is soluble is 158° C. The laminates were then sorted and stored under the conditions provided in Table 4 below. Crystalline Crystal X will begin to from and is conveniently determined after storage for a period of at least two weeks. The crystal structure was determined by XRD in accordance with the materials and methods provided above.

TABLE 4

Preparations of Crystal X at Various Supersaturation Ratios

| [EEHH] wt % | storage temperature (° C.) | supersaturation ratio | crystal structure |
| --- | --- | --- | --- |
| 5 | 80 | 3 | E2-HH |
| 10 | 80 | 6 | E2-HH |
| 5 | 60 | 7 | E2-HH |
| 20 | 80 | 12 | E2-HH |
| 5 | 45 | 14 | Crystal X |
| 10 | 60 | 14 | Crystal X |
| 5 | 32 | 28 | Crystal X |
| 10 | 45 | 28 | Crystal X |
| 20 | 60 | 28 | Crystal X |
| 10 | 32 | 56 | Crystal X |
| 20 | 45 | 56 | Crystal X |
| 20 | 32 | 111 | Crystal X |

Example 3
Preparation of 20 wt % E2-HH in Acrylate Adhesive Matrix Laminates Under Wet Conditions:

Laminates comprising a 20 wt. % estradiol (based on estradiol and adhesive solids) were prepared in accordance with the following procedure. Appropriate amounts of micronized estradiol hemihydrate were added to DURO-TAK® 87-2287 containing ethyl acetate in order to prepare a 20 wt % concentration of estradiol in adhesive solids. Additional ethyl acetate (up to twice the amount of estradiol hemihydrate) was added to the higher concentration samples in order to reduce the wet sample viscosity to aid mixing. The samples were mixed on a rotator overnight. In all cases, the resultant mixture contained a dispersion of crystalline estradiol hemihydrate in wet adhesive. Laminates were drawn down on the release side of 3-EST-A-S242M film to a thickness of approximately 75 microns. The solvent was removed by drying in an oven at 70° C. for 1.5 hours. A second layer of 3-EST-A-S242M film was laminated onto the adhesive, release side contacting adhesive, for storage of the laminates. The laminates were die cut to approximately 10 cm$^2$ pieces. The samples were heat treated in substantial accordance with the teaching of Example 2 above except for the sorting procedure.

In order to permit humidification of the matrix, one of the release liners were removed.

The laminates were then placed in a humidity chamber at 32° C., 80% relative humidity for greater than approximately 72 hours. The crystal structure was determined by XRD in accordance with the materials and methods provided above.

Example 4
Preparation of Crystal X In Polyisobutylene Adhesive Blend (Wet):

A sample of 20 wt. % estradiol in a PIB blend (see materials section, above, for further information) was prepared using a method in substantial accordance with the teaching of Example 1 followed by the heat treatment as described in Example 2 and stored under humidity conditions as in Example 3.

Example 5
Preparation of Crstal X in Silicone (Wet):

A sufficient amount of micronized estradiol hemihydrate is added to Silicone 4201 containing heptane solvent in order to prepare a laminate with 20 wt. % estradiol in adhesive solids. The samples are mixed on a rotator overnight. The resultant mixture contains a dispersion of crystalline estradiol in wet adhesive. A laminate is drawn down on the release side of 3-EST-A-S242M film with a knife at 15 mil wet. The solvent is removed by drying in an oven at 70° C. for 1 hour.

A portion of this laminate is heat treated in substantial accordance with the teaching of Example 2 in an oven at 185° C.±10° C. for 30 minutes and subsequently quenched to room emperature by removing it from the oven. Since the estradiol concentration in this sample is well above the solubility of the drug in Silicone 4201 at the drug melting temperature (0.8 wt. %, as determined by DSC), this sample is multi-phase following heat treatment. The samples were placed under humidity conditions in substantial accordance with the teaching of Example 3.

Example 6
Solubility Experiment with E2-HH and Crystal X

Adhesive matrices containing E2-HH, were prepared in substantial accordance with the teaching of Example 1. Adhesive matrices containing Crystal X crystals were prepared in substantial accordance with the teaching of Examples 2 and 3. The receivers cells comprised substantially pure Durotak adhesive matrices. The donor and receiver matrices were separated from each other by a 10 mil Silastic membrane. One group of the donor-Silastic-receiver laminates were placed in pouches and place in an oven at 32° C. and 60° C ("dry" conditions). The rest of the donor-Silastic-receiver laminates were placed in a dessicator saturated with water vapour at a temperature of 32° C. and 60° C. temperature ("wet" conditions). The samples were allowed to equilibrate for a period of 3 weeks under these conditions.

In order to determine the solubility in the receiver matrices, estradiol was extracted from the receiver matrices in accordance with the following procedure. The samples were removed from the oven and the dessicator and the release liner was removed from the receiver side. In order to facilitate removal of the receiver away from the Silastic membrane and the donor, a release liner was placed on the receiver. The release liner/receiver fraction was removed from the Silastic membrane and weighed. Each sample was then placed in a 1 oz. Qorpak bottle to which was added 25 ml methanol. The samples were then sonicated for 2 hours with occasional shaking. After cooling, the extract was filtered. Two ml of the filtered solution were then analyzed for E2 content in accordance with conventional procedures (method CAS 193).

Example 7
Comparison of Flux of Crystal X and E2-HH In Acrylate Adhesives:

20 wt % acrylate adhesive matrices were prepared in accordance with Example 1. 20 % Crystal X was prepared in accordance with Example 3. The laminates were allowed to equilibrate for a period of 8 weeks to insure complete crystal structureation. Flux was determined as permeation through a 10 mil Silastic membrane as described above. The cumulative release of estradiol into the receiver was determined by HPLC method described above. The average flux over the period was calculated as the cumulative amount of drug in receiver divided by cumulative time. The results are presented in Table 2 hereinabove.

Example 8
Comparison of Flux From Supersaturated Acrylate and PIB Adhesives:

A comparison of the flux obtained from acrylate adhesive matrices containing estradiol hemihydrate, PIB adhesives containing estradiol hemihydrate, acrylate and PIB adhesive matrices supersaturated with estradiol hemihydrate is provided below. The acrylate matrices were prepared in substantial accordance with the teaching of Example 2. The PIB matrices were prepared in substantial accordance with Example 4. In these experiments an aqueous donor was employed with excess E2 hemihydrate as control. A Silastic membrane 10 mil. was introduced between the donor and receiver cells. The receiver fluid was nanopure water, and the duration of the flux experiments as over a period of approximately 2 days at 32° C. A summary of the data obtained is provided in Table 5 below.

TABLE 5

Comparison of Estradiol Flux From Crystal X and E2-HH Formulations in Polyisobutylene and Acrylate Adhesive Matrices

| Sample | average flux ($\mu g/cm^2/hr$) |
| --- | --- |
| aqueous donor | 0.09 |
| PIB E2-HH. 20% | 0.03 |
| Durotak, E2-HH, 20.5% | 0.11 |
| PIB, supersaturated, 20% | 0.06 |
| Durotak, supersaturated 20.5% | 0.39 |

The same value of flux for E2 saturated in water and in Durotak implies that the flux in this study was membrane controlled. That means that the amount of drug crossing the membrane is determined by the thermodynamic activity of the solid drug (being E2-HH in both cases) and the rate limiting step is the membrane. The heat treated samples show a significantly higher initial flux profile due to the high level of supersaturation where still a lot of drug is dissolved. The drop in flux for both PIB and Durotak supersaturated samples indicates that crystals have formed during the flux study. These crystals were confirmed as Crystal X by XRD. The plateau value for the Durotak supersaturated samples shown here is higher than the plateau values obtained in Example 7 (Table 2) because the crystallization of Crystal X is not yet complete within the period under which these flux studies were performed. Once the equilibration is complete, the results obtained are expected to be similar. PIB supersaturated samples demonostrate an increased flux relative to PIB E2-HH systems. However, in these systems, the flux profile is not membrane controlled.

Example 9
Method of Preparing Crystal X In Absence of Adhesive

The following procedure provides a method for the preparation of Crystal X in the absence of a polymeric matrix in contrast to the procedures provided in Examples provided above. A sample of pure micronized E2-HH was placed in an O-ring sealed aluminum or steel DSC (differential scanning calorimeter) pan. No extra water was added to the container. The sample of micronized E2-HH was heated to a temperature in slightly in excess of the melting temperature of micronized E2-HH to insure complete melting of the estradiol crystals. The sample was cooled from the melting temperature to room temperature (25° C.) at a rate of 5° C. per minute. The presence of Crystal X was confirmed by XRD.

We claim:

1. A method for preparing a crystalline form of estradiol characterized by possessing at least one diffraction peak having a 2θ angle of 11.2°±0.2°, 12.7°±0.2°, 17.4°±0.2° or 19.6°±0.2°, said method comprising the steps of:
   a) preparing a supersaturated suspension of estradiol hemihydrate crystals in an adhesive and solvent;
   b) removing the solvent;
   c) heating the suspension to a temperature sufficient to dissolve the estradiol hemihydrate crystals in the adhesive; and
   d) transferring the suspension to conditions wherein the supersaturation ratio is greater than or equal to about 12.

2. A method for preparing a crystalline form of of estradiol characterized by possessing at least one diffraction peak having a 2θ angle of 11.2°±0.2°, 12.7°±0.2°, 17.4°±0.2° or 19.6°±0.2°, said method comprising the steps of:

a) preparing a supersaturated suspension of estradiol hemihydrate crystals in an adhesive and solvent;

b) removing the solvent;

c) heating the suspension of to a temperature sufficient to dissolve the estradiol hemihydrate crystals in the adhesive; and d) transferring the suspension to conditions of approximately 32° C. and 80% relative humidity.

3. A method for preparing a crystalline form of of estradiol characterized by possessing at least one diffraction peak having a 2θ angle of 11.2°±0.2°, 12.7°±0.2°, 17.4°±0.2° or 19.6°±0.2° from micronized estradiol hemihydrate (E2-HH) crystals said method comprising the steps of:

a.) preparing a sample of pure micronized E2-HH in an sealed container in the absence of extraneous water;

b.) heating the sample to the melting temperature of the micronized E2-HH and c.) cooling the sample at a controlled rate so as to form Crystal X.

4. The method of claim 1, further comprising the step of e) incorporating the suspension into a pharmaceutical formulation.

5. The method of claim 4, wherein the pharmaceutical formulation comprises a transdermal drug delivery device.

6. The method of claim 5 wherein the pharmaceutical formulation further comprises a skin permeation enhancer.

7. The method of claim 5, wherein the pharmaceutical formulation further comprises a progestin.

8. The method of claim 1, wherein the adhesive is chosen from the group consisting of acrylates, silicones, and polyisobutylenes.

9. The method of claim 2, further comprising the step of e) incorporating the suspension into a pharmaceutical formulation.

10. The method of claim 9 wherein the pharmaceutical formulation comprises a transdermal drug delivery device.

11. The method of claim 10, wherein the pharmaceutical formulation further comprises a skin permeation enhancer.

12. The method of claim 10, wherein the pharmaceutical formulation further comprises a progestin.

13. The method of claim 2, wherein the adhesive is chosen from the group consisting of acrylates, silicones, and polyisobutylenes.

14. The method of claim 3 wherein the controlled rate of cooling is approximately 5° C. per minute.

15. The method of claim 3, further comprising the step of d) incorporating the sample into a pharmaceutical formulation.

16. The method of claim 15 wherein the pharmaceutical formulation further comprises a pharmaceutical excipient.

17. The method of claim 16, wherein the pharmaceutical formulation comprises tablets.

18. The method of claim 15, wherein the pharmaceutical formulation further comprises a progestin.

* * * * *